(12) United States Patent
Gharibian

(10) Patent No.: US 10,912,466 B2
(45) Date of Patent: Feb. 9, 2021

(54) SMART BLOOD PRESSURE MEASURING SYSTEM (SBPMS)

(71) Applicant: Albrik Levick Gharibian, Glendale, CA (US)

(72) Inventor: Albrik Levick Gharibian, Glendale, CA (US)

(*) Notice: Subject to any disclaimer, the term of this patent is extended or adjusted under 35 U.S.C. 154(b) by 65 days.

(21) Appl. No.: 15/960,512

(22) Filed: Apr. 23, 2018

(65) Prior Publication Data

US 2019/0320915 A1 Oct. 24, 2019

(51) Int. Cl.
| | |
|---|---|
| *G06K 9/00* | (2006.01) |
| *A61B 5/021* | (2006.01) |
| *A61B 5/022* | (2006.01) |
| *A61B 5/026* | (2006.01) |
| *A61B 5/00* | (2006.01) |
| *A61B 5/0402* | (2006.01) |

(52) U.S. Cl.
CPC ......... *A61B 5/02108* (2013.01); *A61B 5/022* (2013.01); *A61B 5/026* (2013.01); *A61B 5/02141* (2013.01); *A61B 5/6824* (2013.01); *A61B 5/0006* (2013.01); *A61B 5/0402* (2013.01); *A61B 5/742* (2013.01)

(58) Field of Classification Search
None
See application file for complete search history.

(56) References Cited

U.S. PATENT DOCUMENTS

| | | | |
|---|---|---|---|
| 2017/0150930 A1* | 6/2017 | Shikii | A61B 5/026 |
| 2018/0042486 A1* | 2/2018 | Yoshizawa | A61B 5/1032 |
| 2018/0177464 A1* | 6/2018 | DeBusschere | A61B 5/1079 |
| 2020/0288996 A1* | 9/2020 | Yoshizawa | A61B 5/02 |

* cited by examiner

*Primary Examiner* — Atiba O Fitzpatrick
(74) *Attorney, Agent, or Firm* — Phil IP Law Inc.; Narek Zohrabyan

(57) ABSTRACT

Systolic and Diastolic Blood Pressure numbers displayed by the use of the Video taking built-in feature in any mobile device. This unique method of displayed Blood Pressure uses a Video Microanalysis Mobile Application to identify the millionth of a meter change in the blood flow through artery. This method further comprising a database for comparison between the identified change in the artery by the Video analysis and the Standard measurement of Cuff or Digital Wrist Blood Pressure measuring devices in mmHg. This method of displaying Blood Pressure is convenient and the measurement can easily be repeated and emailed.

4 Claims, 4 Drawing Sheets

The VMA to start detecting the Rise and the Fall from Zero reference point

SMART BLOOD PRESSURE MEASURING SYSTEM (SBPMS)

CROSS-REFERENCE TO RELATED APPLICATIONS

Please note that two previously submitted applications, in relation to this application dated Apr. 15, 2018, are as follows:

This application claims Priority from the Provisional Application No. 62/124,355 filing date of Dec. 17, 2014, and subsequently from the Non-Provisional patent application Ser. No. 14/757,077 filed on Nov. 16, 2015.

The submitted application Ser. No. 14/757,077 was Utility type, with Micro Entity status, including 8 Claims application, submitted under the same title, Smart Blood Pressure Measuring System (SBPMS).

This application dated Apr. 22, 2018 is a new invention with new Claims.

The two common ideas used between this new submitted invention compare to the application Ser. No. 14/757,077 are the use of a table in a database to compare the two different methods of measuring Systolic Blood Pressure (SBP) and Diastolic Blood Pressure (DBP).

In addition, this new invention has the same Title of invention, namely, Smart Blood Pressure Measuring System (SBPMS) as the previously submitted application Ser. No. 14/757,077.

REFERENCE TO A "SEQUENCE LISTING"

This application dated Apr. 22, 2018 will be submitted via EFS-Web by using the Customer Number 154810 which was provided by the United States Patent Office, ebc_team@USPTO.gov where I obtained my Digital Certificate on Apr. 19, 2018.

BACKGROUND OF THE NEW INVENTION

Smart Blood Pressure Measuring System, abbreviated SBPMS, uses any mobile device to display the Systolic and Diastolic Blood Pressure, (e.g., 120/80 mmHg).

Sound measured from blood flowing through artery was in my prior submitted patent application Ser. No. 14/757,077.

Hence, this application does not use Sound as the input signal, instead I am using "Video Microanalysis Application" abbreviated VMA, with new Claims in this application.

This application is used to analyze the Systolic referring to the "Elevation" or the "Rise" and Diastolic referring to the "Depression" or the "Fall" of the detected pulsation of the Blood Pressure (BP) in any artery.

The user downloads "Video Microanalysis Application" abbreviated VMA, to his/her mobile device.

As the heart pumps blood through the arteries, it creates a pulse that one can feel on the arteries close to the skin surface.

This invention is based on the VMA that detects the Rise and the Fall of the heart pulsation. The VMA Rise and Fall measured values of BP are compared against the Cuff or Digital Wrist BP measuring devices.

The result of these two concurrently measured values populate a Table in the Database named "VMA Database".

The video can be taken from the skin's surface of any hands or external Carotids through the built-in video taking feature of any mobile device.

BRIEF SUMMARY OF THE INVENTION

In order to receive the input signal to the mobile device, an application named, VMA is downloaded to any mobile device. (The VMA is one of the Claims).

The VMA will guide the user through multiple steps to eventually display their measured BP. (This is one of the other Claims).

The peak value of the Rise (Systolic Blood Pressure, SBP) and the Fall value from the from the peak compared to the reference point which will be the surface of the skin will be the value of the Diastolic Blood Pressure DBP measured by the VMA in Micron.

These Rise and the Fall numbers in Micron will be compared to the Rise and the Fall of the Cuff or Digital Wrist in mmHg, which were concurrently measured and tabulated in the VMA Database. (This will be one of other Claims).

These two values will be displayed on the mobile device.

These peak values from the two methods of measurements were taken for every 2 units of increments covering all the possible BP measurements. This means starting from Zero mmHg (millimeters of Mercury) vs. Zero Micron (surface of the Skin) calibrated through 300 mmHg vs. 300 Micron.

These values will be registered in the Video Microanalysis Application cache memory for calculating and processing the final SBP and the DBP.

The captured video from the surface of the skin will last for about 30 seconds. The VMA prompts the user that the 30 seconds need to be repeated, if no Rise or Fall in the captured video of the Artery was detected.

After the input signal of the Rise and the Fall has been identified by the VMA. This Video and the Rise and the Fall in Micron will be saved in the cache memory of the VMA by assigning a memory address.

This is done so that if the user intends to repeat the measurement of the BP the old value will be replaced with the new measured value for the new BP calculation.

The purpose of using the VMA method is to make BP measuring simple compare to the Cuff or Digital Wrist devices.

The advantage of my invention is that the user can simply measure his/her blood pressure using the mobile device and email the results to his/her Doctor, at any time without any need to the Cuff or a Digital wrist BP measuring device.

BRIEF DESCRIPTION OF THE SEVERAL VIEWS OF THE DRAWINGS

The accompanying drawings, which are incorporated in and constitute part this specification, illustrate embodiments of the invention and together with the description explain the principles of the present disclosure.

The embodiments illustrated herein are presently preferred, it being understood, however, that the invention is not limited to the precise arrangements and instrumentalities shown, wherein.

For the populating the VMA Database, concurrent measurements of the SBP and DBP will be taken from different skin type and color to cover all the possible existing BP in Micron vs in mmHg (Millimeters of Mercury).

Figure 1:
FIG. 1. is a photo of my hand taken by my mobile device using the Video capturing feature of my hand by my mobile device. This video captured by the VMA detects the Rise and the Fall of the artery from the surface of the skin, which will be the zero or the reference point of the peak value of the Systolic and the low value of the Diastolic blood pressure.
Figure 2:
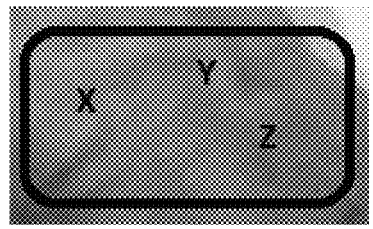

FIG. 2. is pointing to the arteries shown in FIG. 1. The arteries have been denoted by the X, indicating the Surface or the reference point of the measurement. Point Y the Elevation of the artery and point Z the Depression of the artery.

The VMA looks for change in any artery with Elevation and Depression from the surface of the skin where the skin surface will serve as the reference point or the zero axis.

Figure 3:
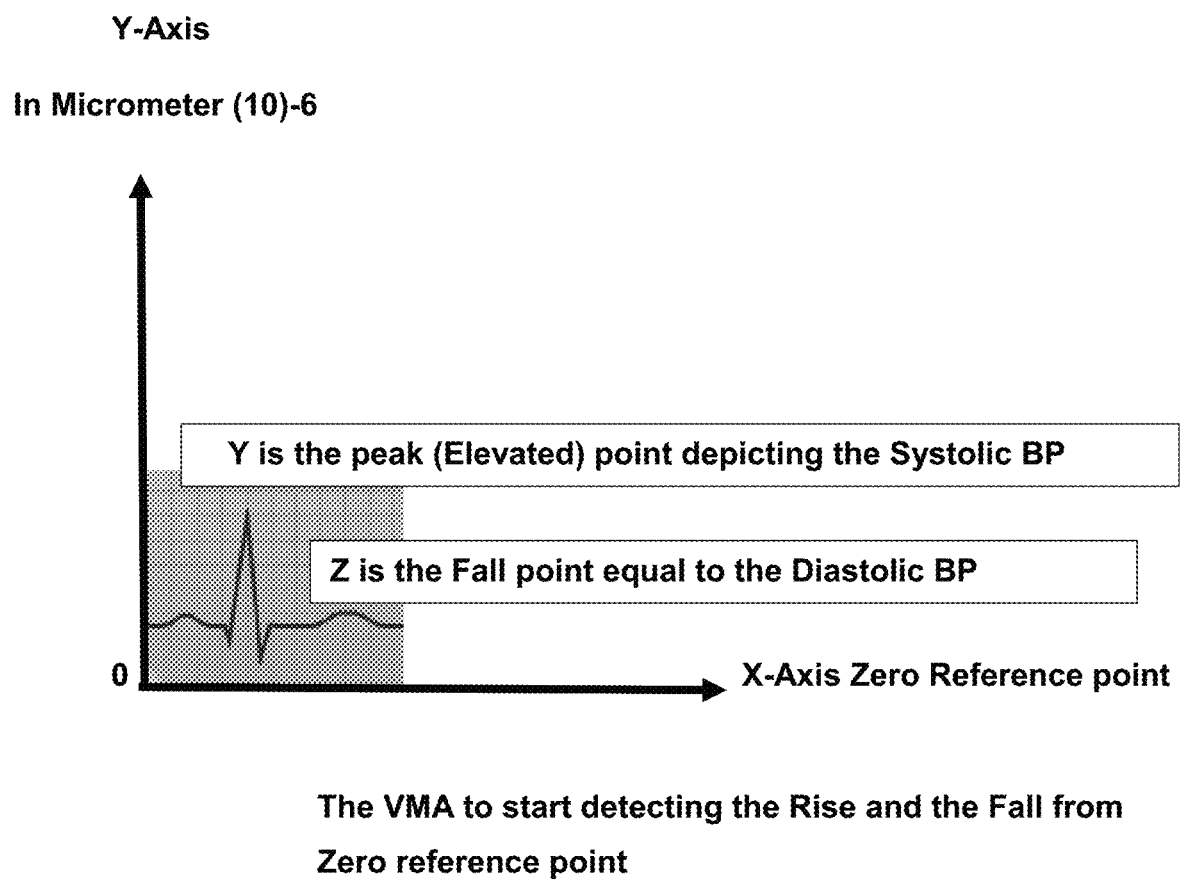

FIG. 3. is a graph or the pulse of artery that the VMA detects with reference to the x axis. The point "Y" is the peak or Elevated or the Rise (Systolic) number (in Micron) and the level "Z' is the Depressed or the Fall level (Diastolic) number in Micron of the pulse.

These two levels are measured from the X-axis, where it is the zero level or the reference point of the two measured levels.

The Diastolic or the "Z" level in the graph is located between the peak amplitude "Y' and above the reference point the X where the X is at Zero Micron.

The Video Microanalysis Application will calculate these "Y" and the "Z" values in Micron with a built-in mathematical waveform analysis and calculation. (This will be one of the claims).

The two pulsation states of arteries, meaning the "Elevation or the Rise" referring to the Systolic and the "Depression or the Fall" the Diastolic calculated by the VMA BP will be saved in the Video Microanalysis Application cache memory.

These numbers in Micron will be compared to the VMA Database for its equivalent numbers in mmHg. As these Systolic and Diastolic numbers have been verified by the VMA to be the exact match in the VMA Database, then the two Systolic and Diastolic numbers will be displayed on the mobile device.

Figure 4:
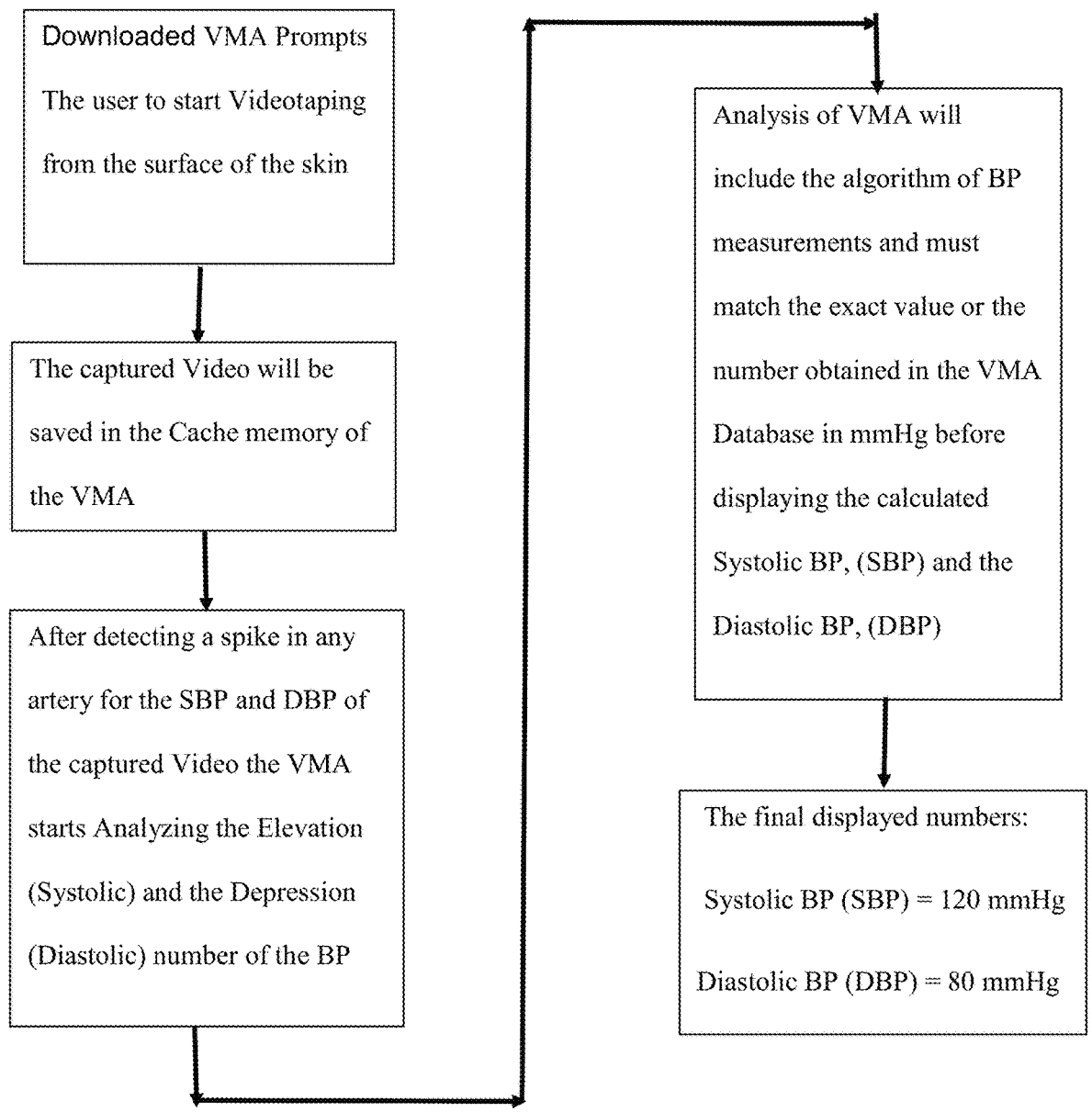

FIG. 4. is flow of the sequence of the events that starts with the prompt issued by the VMA's Interface, which will guide the user through multiple steps to eventually display their measured BP.

These two numbers will be compared to the VMA Database to match the equivalent mmHg BP for the SBP and the DBP.

Figure 5:
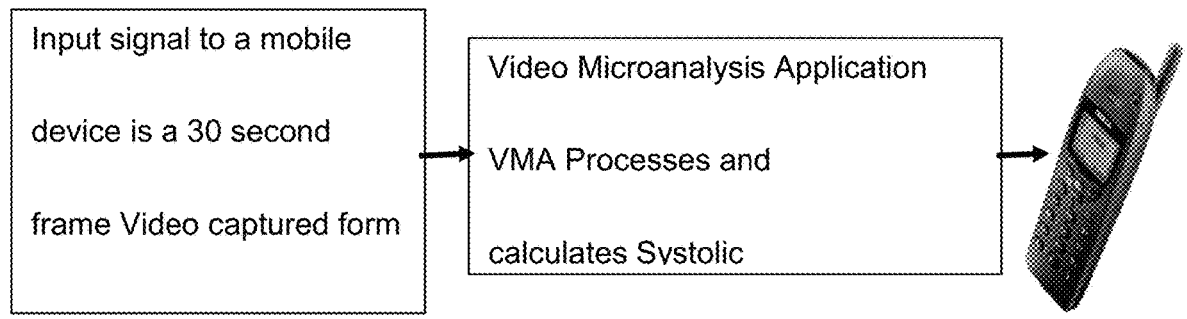

FIG. 5. is the process of the input signal which is the video captured with identified rise and the fall of the artery which gets processed by the VMA in Microns and then compared to the VMA Database with its matched number in mmHg, which is then displayed on the user mobile device.

DETAILED DESCRIPTION OF THE INVENTION

The step one in the VMA is to press the button to start videotaping the surface of the hand skin for about 30 seconds using the built-in feature of any mobile device's video taking capability.

The unit of measurement of the two states the "Rise or Elevation/Fall or Depression" is in Microns, short for Micrometer. This unit of measurement is equal to one millionth of a meter. This is equal to Exponent EXP10 (−6) or $10^{-6}$.

The portion of the video as the VMA looks for the Rise and the Fall of artery shown in FIG. 1, as the Rise "Y" and the Fall "Z" points.

The VMA detected Elevation and the Depression shown in FIG. 2 will be saved in the VMA created cache memory for further Microanalysis in Micrometer.

With the surface of the skin being the reference or the zero point for the Rise and the Fall as shown in the FIG. 3 by analysis of the waveform and calculating and saving the exact Rise and the Fall in the two numbers SBP and the DBP, before comparing these two numbers against the VMA Database.

If no artery elevation or depression is detected the VMA will prompt for the second taking of the video for about 30 seconds.

If the VMA analysis of the change in the artery of the video taken, for example, it is 10 Micrometer, this means the artery was elevated from its rest position of zero to a height of 10 Micrometers.

This highest elevation will be equal to the (top value) Systolic blood pressure SBP and the depressed measured value will be equal to the (low value) for example 5 Micron will be equal to the Diastolic blood pressure DBP as shown in FIG. 3.

The mmHg values are also measured by a cuff or a Digital wrist BP measuring device, where the same measurements were repeated for the VMA application to cover all the possible Blood pressures to populate the VMA Database as shown in the VMA Database below with some numbers.

This means for every value of the elevated and depressed values of the video Microanalysis for Systolic and Diastolic blood pressure in Micron, there will be a corresponding cuff-measured blood pressure value in mmHg.

As the VMA analysis of the waveform is completed with a specific value, for example, Systolic value of 20 Micrometer and Diastolic of 2 Micrometer, the VMA will identify the matching value of the same Cuff measured value that corresponds to the Systolic and Diastolic value.

For example, if the SBP=20 Micron and DBP=2 Micron has been Registered in the memory by the VMA the comparison state of the VMA will be to match the previously measured numbers in mmHg, where as shown in the Table below they are equal to SBP=110 mmHg and the DBP=90 mmHg.

The above two numbers will be displayed on the user mobile device, due to the fact that these two numbers were previously measured to be the SBP and the DBP.

FIGS. 4, and 5 show the flow of the sequence of the events with the input through the output signals, resulted from the Video analysis through to the final compared and exact number in mmHg.

The SBP and DBP are relative measurements. This means the thickness of the skin where the Video is taken has nothing to do with the accuracy of the measurements.

This is also true in the case or Cuff and Digital wrist measuring units that are currently on the market. The BP measured using the standard Cuff or Digital wrist instruments are also relative measurements, where the thickness of the skin is not a factor in the final outcome of the SBP and DBP.

The pre-populated SAMPLE table will be named the "VMA Database".

The following value or numbers in Micron and mmHg are some sample numbers in Micrometer vs. Cuff measured values of SBP and DBP in mmHg.

| VMA DATABASE | | | |
|---|---|---|---|
| Video Analysis values of Systolic & Diastolic in Micrometer | | Cuff-measured values of Systolic & Diastolic in mmHg | |
| VMA SYSTOLIC values in Micron | VMA DIASTOLIC values in Micron | Cuff-measured SYSTOLIC values in mmHg | Cuff-measured DIASTOLIC values in mmHg |
| 10 Micrometer | 8 Micrometer | 100 mmHg | 76 mmHg |
| 16 Micrometer | 6 Micrometer | 106 mmHg | 70 mmHg |
| 20 Micrometer | 2 Micrometer | 110 mmHg | 90 mmHg |
| 26 Micrometer | 4 Micrometer | 120 mmHg | 80 mmHg |
| 6 Micrometer | 2 Micrometer | 92 mmHg | 76 mmHg |
| 12 Micrometer | 4 Micrometer | 94 mmHg | 78 mmHg |

What is claimed is the following:

1. A method for identifying a state of artery by the use of a Video Microanalysis Application (VMA), comprising;
    guiding a user through multiple steps in order to display the user's measured blood pressure, using the VMA which contains an interface where the interface is a sub-component of the VMA;
    detecting rise/elevation and fall/depression in arterial walls measured in micrometers, as blood flows through the arteries while being captured by the VMA;
    capturing a video stream, using a mobile device, that contains a scene of blood flowing through the arteries where the video stream is analyzed to calculate a rise/elevation and a fall/depression of the systolic and diastolic, respectively, with reference to a point on the surface of the skin;
    comparing the calculated rise/elevation and fall/depression results to a database containing correlates of the rise/elevation and fall/depression values enumerating systolic and diastolic values represented in millimeter of mercury (mmHg);
    measuring, continuously or in real-time, the rise/elevation and fall/depression values relative to the reference point that is set to a value of zero; and
    determining a peak value of the arterial rise/elevation and a peak value of the arterial fall/depression in relation to the reference value, where the fall/depression value is lower than the rise/elevation value.

2. The method of claim 1, wherein:
    accessing the database where the systolic and diastolic values are enumerated based on pre-measured systolic and diastolic numbers acquired from usage of other measuring instruments;
    identifying, from the database, equivalent systolic and diastolic blood pressure values in micrometers by comparing and identifying systolic and diastolic matching values in mmHg in increments of two micrometers; and
    displaying the identified systolic and diastolic matching values in mmHg to the user.

3. The method of claim 1, wherein the capturing of the scene in the video stream measures about a 30 second time-frame.

4. The method of claim 1, wherein the calculating of the rise/elevation values and fall/depression values uses a built-in mathematical waveform analysis.

* * * * *